United States Patent [19]

Sudo et al.

[11] Patent Number: 5,208,012
[45] Date of Patent: May 4, 1993

[54] ANTI-INFLAMMATORY OR ANTI-SUNBURN COSMETIC COMPOSITION

[75] Inventors: Mirihiro Sudo, Tokyo; Tomoyasu Muraki, Abiko; Eiji Kawachi, kiryu; Yasushi Kawachi, Ashikaga, all of Japan

[73] Assignee: Daikyo Gomu Seiko Ltd., Tokyo, Japan

[21] Appl. No.: 738,544

[22] Filed: Jul. 31, 1991

[51] Int. Cl.$^5$ .......................... A61K 7/40; A61K 7/42; A61K 7/44; A61K 7/48
[52] U.S. Cl. ........................................ 424/59; 424/47; 424/60; 424/63; 424/69; 424/78.05; 514/845; 514/886; 514/887; 514/937; 514/938; 514/941; 514/943; 514/944; 514/969
[58] Field of Search .................. 514/886, 887; 424/59, 424/60

[56] References Cited

U.S. PATENT DOCUMENTS 3,444,164  5/1969  Luethi et al. .......................... 424/60

Primary Examiner—Dale R. Ore
Attorney, Agent, or Firm—Wenderoth, Lind & Ponack

[57] ABSTRACT

An anti-inflammatory cosmetic composition having a large effect of absorbing and shielding all of UV-A, UV-B and UV-C, small degeneration with the passage of time even upon absorption of light, small influence upon the skin, not lowered effect of absorbing light and high stability for heat is provided. This anti-inflammatory cosmetic composition comprises 0.1 to 20% by weight of a hydroxyaryl-s-triazine compound represented by the following structural formula in a cosmetically acceptable oil carrier:

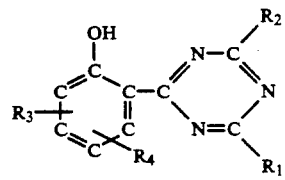

wherein $R_1$ and $R_2$ represent, same or different, hydrogen atoms, chlorine atoms, hydroxyl groups, alkoxy groups of 1 to 18 carbon atoms, aryloxy groups of 6 to 8 carbon atoms or mono- or dialkylamino groups containing 1 to 4 carbon atoms and $R_3$ and $R_4$ represent, same or different, hydrogen atoms, chlorine atoms, alkyl groups of 1 to 8 carbon atoms, methoxy groups or ethoxy groups.

4 Claims, 1 Drawing Sheet

ANTI-INFLAMMATORY OR ANTI-SUNBURN COSMETIC COMPOSITION

BACKGROUND OF THE INVENTION

1. Field of the Invention

This invention relates to an anti-inflammatory or anti-sunburn cosmetic composition.

2. Description of the Prior Art

It is well known that the sunlight and/or lights by artificial light sources, in particular, ultraviolet rays have some influences on the skin. Lights are classified, depending on the wavelengths, into ultraviolet rays (200-400 nm), visible rays having longer wavelengths (400-700 nm) and infrared rays having further longer wavelengths (700 or more nm).

The ultraviolet rays in the shortest wavelength range (200-290 nm) is called "UV-C" and the light having this wavelength range in the sunlight is almost absorbed in the ozone zone, so that it does not reach the earth. However, a quartz mercury lamp radiates a light of the shortest wavelength 185 nm and a sterilizing ray of 253.7 nm and furthermore, UV-C is also radiated from other sources, e.g. discharge tubes of hydrogen or nitrogen, nuclear reactors, etc. This light causes erythema with a dose of 5 to 20 mmJ/cm$^2$.

The ultraviolet rays in the middle wavelength range (290-320 nm) is called "UV-B" which causes erythema, bleb, sunburn upon irradiation for 4 to 20 hours. This wavelength range, generally promoting formation of melanin and causing pigmentation (sunburn) and skin injure, is present in the sunlight, whereby injure of the skin is maximized. An artificial sunlight generally has a wavelength of 320 to 400 nm.

The ultraviolet rays in the longer wavelength range (320-400 nm) is called "UV-A" having an energy of about 20 to 50 mmJ/cm$^2$ and it is considered that this wavelength range instantaneously affects the skin, but does not cause a large change thereon.

However, it has lately been found with the progress of electron microscopes and skin histochemistry that the radiation of UV-B or UV-C tends to not only cause superficially chloasma or melanotic freckle but also reach the derma of the skin and bring on a slightly chronic change in the elastic fibers in the vascular wall or connective tissue, resulting in promotion of degeneration of the interior tissue, promotion of ageing of the skin and cause of cutaneous cancer. Further, it is found that such a phenomenon is proportional to the product of a light energy and radiation time (active energy density) and that UV-A promotes degeneration of the skin by UV-B described above, resulting in a cause of occurrence of cutaneous cancer. Therefore, the protection from this UV-A has become a great problem.

As described above, the so-called anti-inflammatory cosmetic composition comprising a UV shielding agent or UV absorber has been proposed for the purpose of protecting the skin from degeneration by lights, in particular, ultraviolet rays.

As known UV absorbing compounds, there are benzophenone derivatives (Japanese Patent Laid-Open Publication Nos. 108804/1987 and 139158/1988), kojic acid and its derivatives (Japanese Patent Laid-Open Publication No. 188609/1988), esterified compounds of vitamine C (Japanese Patent Laid-Open Publication No. 129212/1987), cinnamic acid derivatives and aminobenzoic acid derivatives (Japanese Patent Publication No. 31021/1977, Japanese Patent Laid-Open Publication Nos. 31023/1977, 35941/1984, 265215/1987 and 231637/1985), dibenzoylmethane derivatives (Japanese Patent Publication No. 6526/1988 and Japanese Patent Laid-Open Publication No. 24061/1987), ethylrutin derivatives (Japanese Patent Laid-Open Publication Nos. 146810/1988) and chalcone derivatives and flavone derivatives (Japanese Patent Laid-Open Publication Nos. 109544/1987 and 96120/1988).

As the light shielding agent, there are used benzophthalides (Japanese Patent Publication Nos. 42167/1983 and 15885/1984) and cosmetic compositions comprising hydrophobic titanium oxide powder in an oily cosmetic base (Japanese Patent Publication Nos. 42167/1983 and 15885/1984).

As a composite cosmetic, there are proposed a composition comprising a UV absorber (benzophenone type, aminobenzoic acid type, salicylate type and vitamine C) added to a sponge-like porous material such as ethylene-vinyl acetate copolymer or polyethylene (Japanese Patent Publication No. 51931/1987), a cosmetic comprising a UV absorber adsorbed on a porous material such as polystyrene and microcapsulated (Japanese Patent Publication No. 31932/1978), an anti-inflammatory composition comprising a UV absorber, fatty acid, amine base and acrylic polymer (Japanese Patent Publication No. 45607/1986), a cosmetic comprising an antioxidant, benzophenone UV absorber and unsaturated oils and fats and a cosmetic comprising urocanic acid and Parsole A (commercial name).

The synthetic compounds of the prior art used as a UV absorber have the problems that the addition quantity to a cosmetic basis is restricted by the solubility in oils, fats and aqueous bases, they have stimulus to the skin, they are deteriorated after absorbing UV to cause change of the UV absorbing capacity with the passage of time and coloration, they are not suitable for use as a cosmetic basis from the sanitary point of view and they have a limitation on the effect of absorbing light.

Titanium oxide, zinc white and iron oxide, as a light shielding agent, in particular, finely divided products or surface-activated products thereof do not absorb ultraviolet rays, nor meet with change of the materials themselves with the passage of time and have little stimulus on the skin. When using the shielding agents capable of shielding visible rays and having a large hiding power, as a cosmetic, they tend to be whitened or excessively colored during use, so that the transparent feeling of the skin is deteriorated. Therefore, the amount thereof to be used is restricted in not only basic cosmetics but also foundation cosmetics, and the shielding agent in a suitable amount for beauty effect does not have a sufficient shielding effect of ultraviolet rays.

Furthermore, the cosmetics of the prior art have only a small absorbing and shielding effect for UV-A having lately been considered as an important problem.

SUMMARY OF THE INVENTION

It is an object of the present invention to provide an anti-inflammatory cosmetic composition with more excellent shielding effect of ultraviolet rays.

It is another object of the present invention to provide an anti-inflammatory cosmetic composition having a large effect of absorbing and shielding all of UV-A, UV-B and UV-C, small degeneration with the passage of time even upon absorption of light, small influence upon the skin, not lowered effect of absorbing light and high stability for heat.

These objects can be attained by an anti-inflammatory or anti-sunburn cosmetic composition comprising 0.1 to 20% by weight of a hydroxyaryl-s-triazine compound represented by the following structural formula in an oily cosmetic basis:

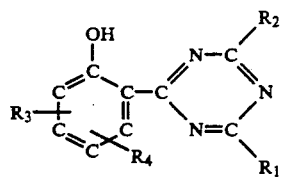

wherein $R_1$ and $R_2$ represent, same or different, hydrogen atoms, chlorine atoms, hydroxyl groups, alkoxy groups of 1 to 18 carbon atoms, aryloxy groups of 6 to 8 carbon atoms or mono- or dialkylamino groups containing 1 to 4 carbon atoms and $R_3$ and $R_4$ represent, same or different, hydrogen atoms, chlorine atoms, alkyl groups of 1 to 8 carbon atoms, methoxy groups or ethoxy groups.

BRIEF DESCRIPTION OF THE DRAWINGS

The accompanying drawings are to illustrate the principle and merits of the present invention in greater detail.

DETAILED DESCRIPTION OF THE INVENTION

Figure 1:
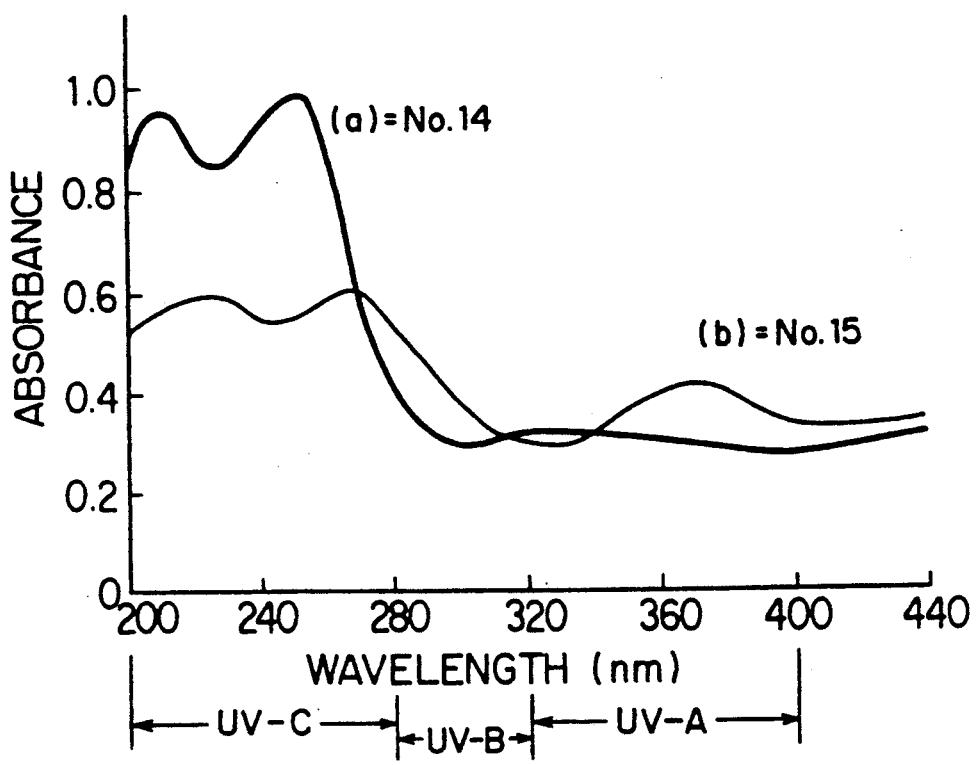
FIG. 1 is a graph showing absorbance curves of ultraviolet rays and high wavelength light by HOAT compound according to the present invention, in which (a) is an absorbance curve of 2,4-dimethoxy-6-(2-hydroxyphenyl)-s-triazine (No. 14) and (b) is that of 2,4-dimethoxy-6-(2-hydroxy-5-methoxyphenyl)-s-triazine (No. 15).

The inventors have made various efforts to provide an anti-inflammatory or anti-sunburn cosmetic composition having a more excellent effect of absorbing and shielding ultraviolet rays than that of the prior art and consequently, have found that the use of a hydroxyaryl-s-triazine compound is very effective for this purpose.

Accordingly, the present invention provides an anti-inflammatory or anti-sunburn cosmetic composition comprising 0.1 to 20% by weight of a hydroxyaryl-s-triazine compound represented by the following structural formula in a cosmetically acceptable oil carrier:

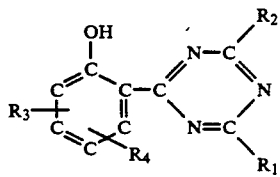

wherein $R_1$ and $R_2$ represent, same or different, hydrogen atoms, chlorine atoms, hydroxyl groups, alkoxy groups of 1 to 18 carbon atoms, aryloxy groups of 6 to 8 carbon atoms or mono- or dialkylamino groups containing 1 to 4 carbon atoms and $R_3$ and $R_4$ represent, same or different, hydrogen atoms, chlorine atoms, alkyl groups of 1 to 8 carbon atoms, methoxy groups or ethoxy groups.

Examples of the hydroxyaryl-s-triazine compound represented by the above described formula (I), which will hereinafter be referred to as "HOAT", are given below without limiting the scope of the present invenetion:

No. 1) 2,4-dichloro-6-(2-hydroxyphenyl)-s-triazine

No. 2) 2-chloro-4-methoxy-6-(2-hydroxyphenyl)-s-triazine

No. 3) 2,4-diphenoxy-6-(2-hydroxyphenyl)-s-triazine
  Melting Point 164°-165° C.

No. 4) 2,4-di(methylphenoxy-6-(2-hydroxymethylphenyl)-s-triazine

No. 5) 2,4-dimethoxy-6-(2-hydroxymethoxy-t-butylphenyl)-s-triazine

No. 6) 2,4-di(dimethylamino)-6-(2-hydroxy-3,5-dimethylphenyl)-s-triazine

No. 7) 2,4-di(methylphenoxy)-6-(2-hydroxyoctylphenyl)-s-triazine

No. 8) 2,4-di(methoxy)-6-(2-hydroxy-5-methylphenyl)-s-triazine
  Melting Point 134°-135° C.
  UV λmax 268, 347 nm No. 9) 2,4-dilauryloxy-6-(2-hydroxy-di-t-butylphenyl)-s-triazine No. 10) 2-phenoxy-4-methoxy-6-(2-hydroxyphenyl)-s-triazine
  Melting Point 150°-151° C.

No. 11) 2-methoxy-4-p-methylphenoxy-6-(2-hydroxyphenyl)-s-triazine

No. 12) 2-dimethylamino-4-methoxy-6-(2-hydroxy-5-methylphenyl)-s-triazine
  Melting Point 137°-138° C.
  UV λmax 262 nm No. 13) 2,4-bis(dimethylamino)-6-(2-hydroxy-5-methylphenyl)-s-triazine
  Melting Point 162°-163° C.
  UV λmax 256 nm No. 14) 2,4-dimethoxy-6-(2-hydroxyphenyl)-s-triazine
  Melting Point 112°-113° C.
  UV λmax 267 nm No. 15) 2,4-dimethoxy-6-(2-hydroxy-5-methoxyphenyl)-s-triazine
  Melting Point 135°-156° C.
  UV λmax 268 nm No. 16) 2,4-dimethoxy-6-(2-hydroxy-5-chlorophenyl)-s-triazine
  Melting Point 145°-146° C.
  UV λmax 350 nm No. 17) 2-[4-methylphenoxy]-6-(2-hydroxy-5-methylphenyl)-s-triazine
  Melting Point 216°-217° C.
  UV λmax 273 nm No. 18) 2,4-dihydroxy-6-(2-hydroxyphenyl)-s-triazine No. 19) 2-phenoxy-4-hydroxy-6-(2-hydroxyphenyl)-s-triazine No. 20) 2,4-bis(dimethylamino)-6-(2-hydroxyphenyl)-s-triazine
  Melting Point 145°-146° C.
  UV λmax 256 nm No. 21) 2-dimethylamino-4-phenoxy-6-(2-hydroxyphenyl)-s-triazine
  Melting Point 147°-148° C.

No. 22) 2-methoxy-4-(p-tolyloxy)-6-(2-hydroxy-5-methylphenyl)-s-triazine

Melting Point 131°–132° C.
UV λmax 271 nm
No. 23) 2,4-bis(tolyloxy)-6-(2-hydroxy-5-methylphenyl)-s-triazine
Melting Point 158°–159° C.

Synthesis of HOAT compound of the present invention, as described above, is generally carried out by reacting, for example, cyanuryl trichloride ($C_3Cl_3N_3$) as a raw material with an alcohol, amine or aryl compound to remove and replace the chlorine and to obtain alcohol-, amine- and aryl-substituted chloro-s-triazine, subjecting a phenol and the chloro-s-triazine to methanol refluxing to remove hydrochloric acid (replacement of chlorine), thus obtaining an oxyaryl-s-triazine, and irradiating an alcoholic solution of the oxyaryl-s-triazine with ultraviolet rays to effect rearrangement reaction and obtain the HOAT compound. This is preferably purified by recrystallization.

The anti-inflammatory cosmetic of the present invention is obtained, as a formulation, by adding 0.1 to 20% by weight of the above described HOAT compound to a cosmetically acceptable oil carrier and the formulation can be any type of ointment, cream, latex, lotion, cataplasm, spray, oily agent, etc.

In the present invention, as the oily cosmetic basis, there can be used known bases described in Notification Nos. 322, 377 and 209 of the Ministry of Welfare, "Japan Cosmetic Raw Material Dictionary (Nippon Keshohin Genryo Jiten)" and the like, for example, vegetable oils, synthetic oils, mineral oils, humidity retention agents, adhesive agents, preservation agents, solvents, emulsifiers, etc.

Examples of the vegetable oil are olive oil, tsubaki oil, cotton seed oil, castor oil, soybean oil, coconut oil, cacao butter, spermaceti, lanolin, beeswax, carnauba wax, hardened oil, stearic acid or salts thereof with Zn, Ca, Mg and Al or butyl ester thereof, myristic acid or salts thereof with Zn and Mg or isopropyl ester thereof, palmitic acid or salt thereof with Zn or isopropyl ester thereof, ascorbic acid, behenic acid, olefinic acid, alcohols of oleyl, cetyl, stearyl, laurel, etc.

Examples of the synthetic oil are glycerol squalenemonostearate, synthetic ester oils, synthetic polyether oils, malic acid esters, sorbitan monooleate, lanolin and hydrogenated products thereof.

Examples of the mineral oil are paraffin, vaseline, liquid paraffin, microcrystalline wax, etc.

Examples of the humidity retention agent are glycerol, propylene glycol, sorbitol, polyethylene glycols, diethylene glycol, propylene glycol, sodium pyrrolidonecarboxylate, etc.

Examples of the adhesive agent are polyvinyl alcohol, carboxymethyl cellulose, sodium salt or propylene glycol ester of alginic acid, rubbers, celluloses, etc.

Examples of the preservation agent are benzoic acid, sorbic acid, dehydroacetic acid, p-oxybenzoic acid esters, camphor, etc.

Examples of the solvent are ethanol, acetone, ethyl acetate, butyl acetate, isopropyl alcohol, purified water, etc.

Examples of the emulsifiers are polyglycerol fatty acid esters, polyoxyethylene lanolin derivatives, polyoxyethylene sorbitan fatty acid esters, polyoxyethylene polyoxypropylene alkyl ethers, polyoxyethylene sorbitol fatty acid esters, soaps, cane sugar fatty acid esters, sorbitan fatty acid esters, propylene glycol fatty acid esters, etc.

The anti-inflammatory cosmetic composition of the present invention comprises optionally known ultraviolet absorbers, in particular, ultraviolet shielding agents in addition to the HAOT compounds and oily cosmetic bases.

As the ultraviolet shielding to be jointly used there are used, for example, titanium oxide (including special finely powdered one, in particular, surface-treated one) and finely powdered or surface-treated zinc white or iron oxide. In the cosmetic of the present invention, the ultraviolet ray shielding agent is preferably present in a proportion of at most 1 part to 100 parts by weight of the composition.

As the ultraviolet ray absorber to be jointly used, there are benzotriazoles, benzophenones and the like.

Examples of the benzotriazole are 2-(2'-hydroxy-5'-methylphenyl)benzotriazole, 2-(2'-hydroxy-3'-t-butyl-5'-methylphenyl)-5-chlorobenzotriazole, 2-(2'-hydroxy-3',5'-di-t-butyl-5'-butylphenyl)-5-chlorobenzotriazole, 2-(2'-hydroxy-3',5'-di-t-butyl-5'-butylphenyl)benzotriazole, 2-(2'-hydroxy-4'-n-octoxyphenyl)benzotriazole, 2-phenylbenzoimidazole-5-sulfonic acid and the like.

Examples of the benzophenone are 2-hydroxy-4-methoxybenzophenone, 2-hydroxy-4-methoxy-2'-carboxybenzophenone, 2-hydroxy-4-octoxybenzophenone, 2,2'-dihydroxy-4-methoxybenzophenone, 2,4-dihydroxybenzophenone, 2,2'-dihydroxy-4,4'-dimethoxybenzophenone, 2,2'-dihydroxy-4,4'-dimethoxy-5-sulfobenzophenone or sodium salt thereof, 2-hydroxy-4-methoxybenzophenone-5-sulfonic acid, 2-hydroxy-4-octadecyloxybenzophenone, 2,2',4,4'-tetrahydroxybenzophenone, 4-dodecyloxy-4-hydroxybenzophenone, 4-hydroxy-4-(2-hydroxy-3-methacryloxy)propoxybenzophenone, 4-phenylbenzophenone-2'-carboxylic acid isooctyl ester, 2,4-di-t-butylphenyl-3,5-di-t-butylhydroxybenzophenone and the like.

Examples of the benzoic acid compound are methyl o-benzoylbenzoate, p-aminobenzoic acid (PABA), glycerol p-aminobenzoate, p-dimethyl aminobenzoate, 2-ethylhexylethyl p-dimethylbenzoate (octyl PABA), ethyl 4-bis-(hydroxypropyl)aminobenzoate, methyl o-aminobenzoate and the like.

Examples of cinnamic acid esters or other esters are benzyl cinnamate, diethanolamine salt of p-methoxycinnamic acid, 2-ethylhexyl p-methxoycinnamate, isopropyl p-methoxycinnamate, gallic acid oleic acid triester, 2ethylhexyl salicylate, 3,3,5-trimethylcyclohexyl salicylate, triethanolamine salt of salicylic acid, p-t-butylphenyl salicylate, 2-ethylhexyl 2-cyano-3, 3-diphenylacrylate, 2-ethylhexyl 3-cyano-3,3'-diphenylacrylate and the like.

Furthermore, there are given oxybenzone, camphor or its sodium sulfonate, 2-phenyl-5-methylbenzoxazole, p-methylbenzylidene-4-(1,1-diethanolmehylethyl)-4'-methoxydibenzoylmethane (-commercial name- Barzole 1798), butylhexyl p-dimethaneaminobenzoate, $\alpha,\beta$-di(p-methoxycinnamoyl)-$\alpha$'-(2-ethylhexanoyl)-glycerol, 2-phenylbenzimidazole-5-sulfonic acid, 5-benz-4-hydroxy-2-methoxybenzenesulfonic acid, urocanic acid and the like.

As vitamins, there are other ascorbic acids, vitamin A oil, vitamin E acetate, vitamin $A_1$, $A_2$, $A_3$, $B_2$, $B_{12}$, vitamin C sulfate, vitamin C dipalmitate, etc.

In the cosmetic composition of the present invention, known antioxidants can preferably be used jointly for the purpose of stabilizing the a cosmetically acceptable oil carrier of the present invention with other additives such as pH regulators, cosmetic fillers, sweetening agents, coloring matters, perfumes, etc.

Examples of the antioxidant are isoascorbic acid, butylhydroxyanisole, dibutylhydroxyanisole, dibutylhydroxytoluene, propyl gallate, tocopherol, sesamol, flavone derivatives, guaiac butter and the like.

As the pH regulator, there are used citric acid, tartaric acid, hydrochloric acid, etc. as an acidic agent, and sodium hydroxide, potassium hydroxide, aqueous ammonia, soaps, etc. as an alkaline agent.

As the cosmetic filler, there are used bentonite, talc, mica, sodium sulfate, barium sulfate, kaolin, calcium sulfate, silica, magnesium carbonate, etc.

As the sweetening agent, there are used saccharin, grape sugar, refined sugar, synthetic sugar, etc. and as the matter, there are used Sensitizing Element 101 giving blue green or white and Edible Color No. 1 and No. 2 giving blueness.

As occasin demands, perfumes can be added.

The anti-inflammatory cosmetic composition of the present invention comprising a HOAT compound, a cosmetically acceptable oil carrier and optionally additives can be used in any form of ointments, creams (vanishing type, neutral type, cold type), emulsions (water-in-oil (w/o) type, oil-in-water (o/w) type), water-enriched latexes (purified water 70–80% by weight), toilet powders (paste powder, solid powder, face powder), sprays, lotions and the like.

In the HOAT compound of the present invention, as a predominant component of the light degradation inhibitor, the phenol group and s-triazine group form such a bonding structure that three carbon atoms, nitrogen atom, hydrogen atom and oxygen atom are brought into excited state by ultraviolet rays and proton movement in the molecule rapidly occurs among these atoms, whereby the tautomerism is rapidly caused, which continues for a long period of time, and the light wavelengths are converted into heat. The absorption (shielding) is not only strong, but also extends to longer wavelengths. That is, not only UV-C and UV-B but also UV-A are absorbed and visible rays are also shielded to be converted into heat energy.

FIG. 1 shows results of measurement of the absorbance. This phenomenon is somewhat different from that of the compounds of the prior art, known as an age resistor or light-shielding agent. Therefore, the HOAT compound of the present invention is capable of absorbing and shielding not only ultraviolet rays but also lights in the longer wavelength range. Furthermore, this compound has such a large absorbing and shielding effect that even the use of it in a small amount, i.e. 0.1% by weight based on a cosmetically acceptable oil carrier is effective for the purpose of the present invnetion.

Figure 2:
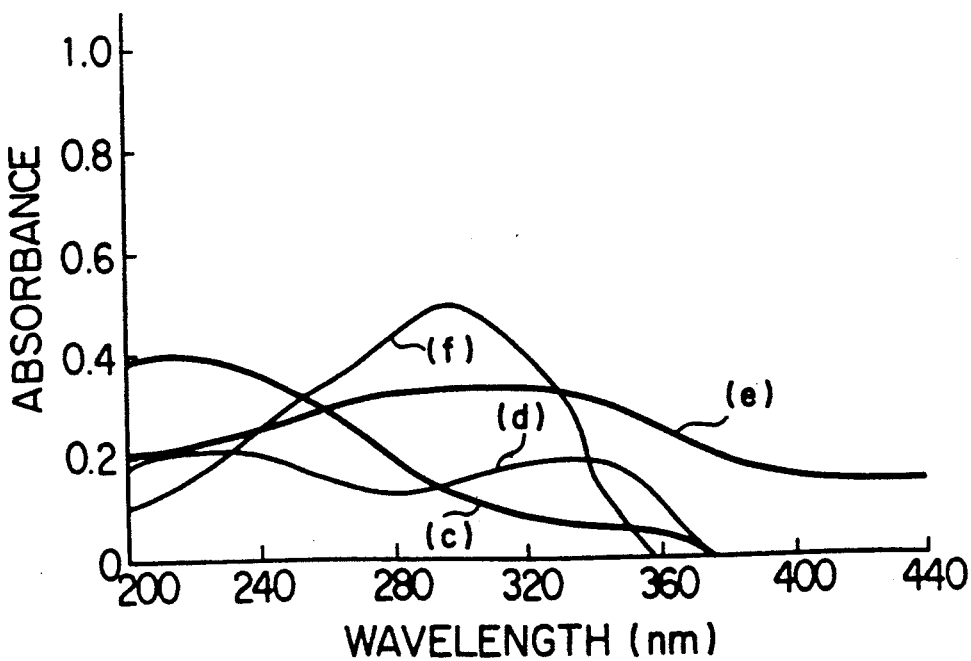
FIG. 2 is a graph showing absorbance curves of the prior art ultraviolet absorber and shielding agent, in which (c) is an absorbance curve of 2-hydroxy-4-methoxybenzophenone, (d) is that of 2-(2'-hydroxy-5'-methylphenyl)benzotriazole, (e) is that of a special fine powder titanium oxide and (f) is that of isopropyl p-methoxycinnamate.

Up to the present time, titanium oxide has been used as an absorbing agent of UV-A for an anti-inflammatory cosmetic composition, but titanium oxide itself is a white pigment and has a disadvantage of opaqueness, as apparent from the absorption spectrum shown in FIG. 2.

On the other hand, the HOAT compound of the present invention has no influence upon the transparency, and in addition, it has such a large compatibleness with a cosmetically acceptable oil carrier as described above that even when using a large amount thereof, i.e. 20% by weight, crystallization hardly take place and the addition amount can thus be increased to obtain a larger light absorption and light-shielding effect.

As described before, UV-A has not been considered to cause a large change on the skin, but of late, UV-A has been considered to cause cutaneous cancer in addition to deterioration of the skin. Since the HOAT compound of the present invention is capable of absorbing UV-A and converting into heat, not only the anti-inflammatory effect is large, but also healthy effects, e.g. of preventing cancer are given.

The following examples are given in order to illustrate the present invention in detail without limiting the same.

EXAMPLE 1

Light Transmission Test for Pig Skin.

5% by weight of each of 2,4-bis(dimethylamino)-6-(2-hydroxy-5-methylphenyl)-s-triazine (HOAT compound of the present invention, No. 13) and 2,4-dimethoxy-6-(2-hydroxy-5-methoxyphenyl)-s-triazine (No. 15) was added, blended, coated onto the surface of a pig skin, cut in piece, with an area of 10 mm×5 mm, irradiated by ultraviolet rays (light source: 5 kw) and then subjected to measurement of the radiated light transmission of the skin by CRN-Diffraction Grating manufactured by Nippon Bunko KK [according to the method described in "Skin Transmission (Hifu Tokasei)" -Nippon Hifuka Gakkai No. 61, Report of Tokyo District Meeting-].

Similar measurements were carried out as to samples using the coating-free pig skin as a blank test and using propylene glycol containing 5% by weight of titanium oxide as a comparative test, thus obtaining results shown in Table 1. As evident from the results, the products of the present invention give a less light transmission and a substantially comparable shielding ratio of ultraviolet rays to titanium oxide.

TABLE 1

| Example | Wavelength (nm) | | | | | | | |
|---|---|---|---|---|---|---|---|---|
| | 280 | 300 | 320 | 340 | 360 | 380 | 400 | Total |
| Blank | | | | | | | | |
| Only Pig Skin | 0 | 10 | 22 | 27 | 32 | 38 | 38 | |
| | (100) | (100) | (100) | (100) | (100) | (100) | (100) | (700) |
| Example 1-1 | | | | | | | | |
| HOAT No. 13 | 0 | 5 | 7 | 8 | 7 | 8 | 10 | |
| | | (50) | (32) | (30) | (22) | (21) | (26) | (181) |
| Example 1-2 | | | | | | | | |
| HOAT No. 15 | 0 | 4 | 5 | 7 | 9 | 11 | 12 | |
| | | (40) | (23) | (26) | (28) | (29) | (32) | (178) |
| Comparative Example | | | | | | | | |
| Titanium Oxide 5 wt % | 0 | 4 | 5 | 6 | 8 | 10 | 16 | |
| | | (40) | (23) | (22) | (25) | (26) | (42) | (178) |

Note: ( ) shows the UV relative transmission (%) when the transmission of Blank = 100% at each wavelength.

EXAMPLE 2

Composition

| (A) 2,4-dimethoxy-6-(2-hydroxy-5-methoxyphenyl)-s-triazine (No. 15) | 5.5 parts |
|---|---|
| Solid Parrafin | 4.8 |
| Microcrystalline Wax | 3.2 |
| Beeswax | 4.8 |
| Vaseline | 9.6 |
| Liquid Paraffin | 35.6 |
| Butylhydroxyanisole | 0.3 |
| (B) Sorbitan Sesquioleate | 3.2 |
| Polyoxyethylene Sorbitan Monooleate | 0.8 |
| Potassium Stearate | 0.3 |
| Purified Water | 31.4 |
| (C) Perfume | 0.5 |
| Total | 100.0 parts |

Composition (A) was mixed and heated with stirring at about 80° C.

Composition (B) was charged in another vessel and heated at 80° C. with stirring. Composition (A) was rapidly stirred in a homomixer, to which Composition (B) was gradually added to render creamy, and the mixture was cooled to 40° C., at which Composition (C) was added thereto and stirred to obtain a product. The thus obtained product of the present invention was subjected to the following test:

Animal Skin Stimulus Test

According to Draize's method, 0.5 g of the above described product sample was coated onto a batch piece and pasted on the skin of the back of a white rabbit, from which fur had been pulled out. The rabbit was covered with a rubber cloth, the batch piece was peeled off after passage of 24 hours and 72 hours and the state of the skin was judged referring to the following stimulus cards:

Erythema: no erythema (0); very slight erythema (1); visible erythema (2); medium to severe erythema (3); severe erythema and light skin formation (4)

Edema: no edema (0); very slight edema (1); slight edema (2); medium edema (3); severe edema (4)

The product of the present invention was in the range of erythema 0 to 1 and edema 0.

EXAMPLE 3

Composition

| 2-methoxy-4-(p-tolyloxy)-6-(2-hydroxy-5-methylphenyl)-s-triazine (No. 22) | 8 g |
|---|---|
| Triglyceride of octanoic acid and decanoic acid | 26 |
| Glycerol Stearate | 6 |
| Polyethylene Glycol Stearate | 6 |
| Stearic Acid | 2 |
| Cetyl Alcohol | 1.2 |
| Lanolin | 4 |
| Silicone Oil | 1 |
| Methyl p-Hydroxybenzoate | 0.3 |
| Propylene Glycol | 2 |
| Triethanolamine | 0.1 |
| Purified Water | 43 |
| Perfume | 0.4 |
| Total | 100.0 g |

EXAMPLE 4

| Anti-inflammatory Cream | parts |
|---|---|
| (A) 2,4-diphenoxy-6-(2-hydroxyphenyl)-s-triazine (No. 3) | 2.0 |
| 2-Ethylhexyl p-Dimethylaminobenzoate | 3.0 |
| Liquid Paraffin | 38.0 |
| Cetyl Alcohol | 1.5 |
| Beeswax | 6.0 |
| Stearic Acid | 2.0 |
| Polyoxyethylene Cetyl Alcohol | 1.5 |
| Sorbitan Monostearate | 2.5 |
| Dibutylhydroxytoluene | 0.5 |
| Preservatives | 0.5 |
| (B) 10% Caustic Soda | 1.0 |
| Purified Water | 30.2 |
| (C) Glycerol | 6.0 |
| Finely Powdered Titanium Oxide (rutile) | 5.0 |
| (D) Perfume | 0.3 |
| Total | 100.0 |

Composition (A) was mixed, heated, solubilized and heated at about 80° C. and Composition (B) was charged in another vessel and heated at 75° C. (B) was added to (A) with agitation to form an emulsion, cooled at 50° C. at which Composition (D) was added and finally, Composition (C) was added thereto. The mixture was then treated in a roll mill to render creamy.

EXAMPLE 5

Anti-inflammatory Cream

| 2,4-bis(tolyloxy)-6-(2-hydroxy-5-methylphenyl)-s-triazine (No. 23) | 2.5 g |
|---|---|
| 2-Ethylhexyl 4-(Dimethylamino)benzoate | 1.0 |
| Purified Water | 55.0 |
| A-C Polyethylene | 5.5 |
| Propylene Glycol | 5.0 |
| Liquid Parafffin or Squalene | 20.8 |
| Sesame Oil | 2.0 |
| Cacao Butter | 2.0 |
| Polyoxyethylene Polyoxypropylene Glycol | 2.46 |
| Polyoxyethylene (3) Oleyl Ether | 3.5 |
| Butyl p-oxybenzoate | 0.2 |
| Butylhydroxyanisole | 0.02 |
| Perfume | 0.02 |
| Total | 100.0 |

EXAMPLE 6

Anti-inflammatory Cream

| 2,4-bis(tolyloxy)-6-(2-hydroxy-5-methylphenyl)-s-triazine (No. 23) | 1.1 g |
|---|---|
| 2,2'-dihydroxy-4-methoxybenzophenone | 2.5 |
| 2-ethylhexyl 4,4-(dimethylamino)benzoate | 1.0 |
| Purified Water | 50.0 |
| A-C Polyethylene | 3.5 |
| Propylene Glycol | 7.0 |
| Liquid Paraffin or Squalene | 15.5 |
| Sesame Oil | 4.0 |
| Octyl Palmitate | 7.0 |
| Cacao Butter | 2.0 |
| Polyoxyethylene Polyoxypropylene Glycol | 2.66 |
| Polyoxyethylene (3) Oleyl Ether | 3.5 |
| Butyl p-oxybenzoate | 0.2 |
| Butylhydroxyanisole | 0.02 |
| Perfume | 0.02 |
| Total | 100.0 |

EXAMPLE 7

Anti-inflammatory Cream

| | | |
|---|---|---|
| (A) | 2-methoxy-4-diphenoxy-6-(2-hydroxyphenyl)-s-triazine (No. 10) | 2.0 g |
| | 2-hydroxy-4-methoxybenzophenone | 0.5 |
| | Vitamin C Dipalmitate | 1.0 |
| | Cetyl Alcohol | 2.0 |
| | Beeswax | 5.0 |
| | Liquid Paraffin | 7.0 |
| | Olive Oil | 18.0 |
| | Stearic Acid | 7.0 |
| | Sorbitan Monostearate | 4.0 |
| | Sorbitan Polyoxyethylene Monostearate | 4.0 |
| (B) | Propylene Glycol | 10.0 |
| | Ascorbic Acid Ester | 2.0 |
| | Purified Water | 37.0 |
| | Propyl Gallate | 0.1 |
| | Perfume | 0.4 |
| | Total | 100.0 |

EXAMPLE 8

Anti-inflammatory Cream

| | | |
|---|---|---|
| (A) | 2-[4-methylphenoxyl]-6-(2-hydroxy-5-methylphenyl)-s-triazine (No. 17) | 8.0 g |
| | Glycerine Monostearate | 6.0 |
| | Polyethylene Glycerine Sterate | 2.0 |
| | Stearic Acid | Glycol |
| | Cetyl Alcohol | 1.2 |
| | Lanolin | 4.0 |
| | Triglyceride of octanoic acid and decanoic acid | 31.0 |
| | Silicone Oil | 15.0 |
| (B) | Methyl p-Benozoate | 0.4 |
| | Propylene Glycol | 2.0 |
| | Triethanolamine | 0.1 |
| | Purified Water | 41.4 |
| | Perfume | 0.4 |
| | Total | 100.0 |

EXAMPLE 9

Anti-inflammatory Pack

| | | |
|---|---|---|
| (A) | 2,4-dimethoxy-6-(2-hydroxyphenyl)-s-triazine (No. 14) | 1.0 g |
| | 2,2-dihyxroxy-4,4'-dimethoxy-5-sulfobenzophenone | 1.0 |
| | OLive Oil | 8.0 |
| | Vitamin C | 2.5 |
| | Beeswax | 5.0 |
| (B) | Titanium Oxide (fine powder) | 4.0 |
| | Zinc WHite (fine powder) | 5.0 |
| | Vinyl Acetate Resin Emulsion (50% by weight) | 15.0 |
| | Polyvinyl Alcohol | 10.0 |
| | Purified Water | 30.0 |
| | Sorbitol | 8.0 |
| | Kaolin | 8.0 |
| (C) | Ethyl Alcohol | 2.0 |
| | Perfume | 0.5 |
| | | 100.0 |

Compositions (A) and (B) were added, heated at about 70° C., uniformly mixed and cooled at about 50° C., at whic Composition (C) was added thereto and stirred to obtain a pack.

EXAMPLE 10

Anti-inflammatory Powder

| | |
|---|---|
| 2,4-dilauryloxy-6-(2-hydroxy-di-t-butylphenyl)-s-triazine (No. 9) | 12.0 g |
| Isooctyl 4-phenylbenzophenone-2'-carboxylate | 3.0 |
| Titanium Oxide | 10.0 |
| Talc | 20.0 |
| Liquid Paraffin | 8.0 |
| Beeswax | 5.0 |
| Mica | 28.0 |
| Glycerol | 3.0 |
| Isostearyl Malate | 2.0 |
| Oxysorbitan Sesquioleate | 3.0 |
| Hexyl Laurate | 5.0 |
| Perfume | suitable |
| Total | 100.0 |

According to the above described recipe, all the components were charged in a mixer, stirred and mixed, to which the perfume was added, and the mixture was further stirred and mixed, and subjected to press-packing to prepare an anti-inflammatory powder.

EXAMPLE 11

Anti-inflammatory Latex

| | | |
|---|---|---|
| (A) | 2,4-di(methoxy)-6-(2-hydroxy-5-methylphenyl)-s-triazine (No. 8) | 3.0 g |
| | Sodium 2-hydroxy-4,4'-methoxybenzophenone-5-sulfonate | 2.0 |
| | Stearic Acid | 2.0 |
| | Cetanol | 1.5 |
| | Lanolin Alcohol | 2.0 |
| | Liquid Paraffin | 10.0 |
| | Polyoxyethylene Monooleate (10 E O) | 2.0 |
| | Propylene Glycol Alginate | 2.0 |
| | Dibutylhydroxy Toluene | 0.5 |
| (B) | Glycerol | 5.0 |
| | Propylene Glycol | 5.0 |
| | Triethanolamine | 1.0 |
| | Vitamin C Sulfate | 0.2 |
| | Purified Water | 63.0 |
| | Benzoic Acid | 0.5 |
| (C) | Perfume | 0.3 |
| | Total | 100.0 |

Compositions (A) and (B) were individually heated at about 70° C. in separate vessels. The phase (B) was strongly stirred in a homomixer, to which (A) was gradually added, and the mxiture was cooled to room temperature, at which the perfume was added.

EXAMPLE 12

Anti-inflammatory Latex

| | | |
|---|---|---|
| (A) | 2,4-dimethoxy-6-(2-hydroxy-5-methoxyphenyl)-s-triazine (No. 15) | 0.3 g |
| | α-Tocopherol Acetate | 0.5 |
| | δ-Tocopherol | 0.1 |
| | Beeswax | 1.0 |
| | Cetanol | 1.0 |
| | Stearic Acid | 2.0 |
| | Liquid Paraffin | 7.0 |
| | Olive Oil | 3.0 |
| | Polyoxyethylene Monooleate (10 E O) | 3.0 |
| | Polyoxyethylene Sorbitan Fatty Acid Ester | 2.0 |
| (B) | Glycerol | 4.0 |
| | Propylene Glycol | 4.0 |
| | Triethanolamine | 1.0 |
| | Vitamin C Sulfate | 0.3 |
| | Purified Water | 69.0 |
| | Propylene Glycol Alginate | 1.0 |

| | -continued | |
|---|---|---|
| | p-Benzoic Acid Ester | 0.5 |
| (C) | Perfume | 0.3 |
| | Total | 100.0 |

The above described formulation (B) was mixed and heated at 70° C., to which the above described formulation (A), similarly mixed and heated at 70° C., was added, and the mixture was uniformly emulsified in a homomixer, cooled and mixed with the perfume to prepare a product.

EXAMPLE 13

(A) Anti-inflammatory Latex (Oil-in-Water type)

| | | |
|---|---|---|
| | 2,4-bis(dimethylamino)-6-(2-hydroxyphenyl)-s-triazine (No. 20) | 1.0 g |
| | Diethanolamine p-Methoxycinnamate | 0.5 |
| | Triethanolamine Salicylate | 0.5 |
| | 2-(2'-hydroxy-5'-methylphenyl)benzotriazole | 1.0 |
| | Glycerol Monostearate of Self-emulsified Type | 1.0 |
| | Cetanol | 1.0 |
| | Silicone Oil | 2.0 |
| | Stearic Acid | 2.0 |
| | Liquid Paraffin | 10.0 |
| (B) | Purified Water | 70.85 |
| | Triethanolamine | 1.0 |
| | 1,3-butylene glycol | 5.0 |
| | Titanium Oxide | 3.0 |
| | Organic Pigment | 0.05 |
| | Bentonite | 0.5 |
| | Preservatives | 0.3 |
| (C) | Perfume | 0.3 |
| | Total | 100.0 |

Composition (A) was heated, solubilized and heated at about 80° C., while Composition (B) was heated, solubilized, uniformly dispersed and heated at 78° C. (A) was gradually added to (B) while stirring, emulsified, cooled while stirring, to which Composition (C) was added, and the mixture was cooled to room temperature to obtain an anti-inflammatory latex of O/W type.

EXAMPLE 14

Anti-inflammatory Latex

| | |
|---|---|
| 2,4-bis(dimethylamino)-6-(2-hydroxy-5-methylphenyl)-s-triazine (No. 13) | 5.0 g |
| Cetyl Stearyl Alcohol | 2.0 |
| Cetyl Alcohol | 2.0 |
| Vaseline Oil | 20.0 |
| Lanolin | 4.0 |
| Stearic Acid | 0.5 |
| Silicone Oil | 0.3 |
| Propyl p-Hydroxybenozoate | 0.4 |
| Glycerol | 5.0 |
| Polyacrylic Acid | 0.15 |
| Triethanolamine | 0.2 |

| | -continued | |
|---|---|---|
| | Purified Water | 60.15 |
| | Perfume | 0.3 |
| | Total | 100.0 |

The anti-inflammatory cosmetic composition of the present invention has the feature that it has a function of protecting the skin from lights, in particular, any wavelengths of UV-A, UV-B and UV-C of ultraviolet rays and a particularly large effect of absorbing UV-A. Since the specified compound of the present invention has no bad influence upon the skin and has a large compatibility with an oily cosmetic basis, furthermore, the amount to be added can freely be varied and the protecting effect can largely be improved over the prior art articles while maintaining the transparency.

What is claimed is:

1. An anti-inflammatory or anti-sunburn cosmetic composition comprising 0.1 to 20% by weight of a hydroxyaryl-s-triazine compound of the following structural formula (I) in a cosmetically acceptable oil carrier:

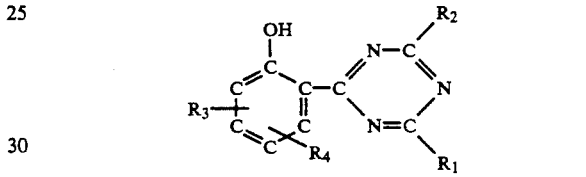

wherein $R_1$ and $R_2$ are the same or different, hydrogen atoms, chlorine atoms, hydroxyl groups, alkoxy groups of 1 to 18 carbon atoms, aryloxy groups of 6 to 8 carbon atoms or mono- or dialkylamino groups containing 1 to 4 carbon atoms and $R_3$ and $R_4$ represent, same or different, hydrogen atoms, chlorine atoms, alkyl groups of 1 to 8 carbon atoms, methoxy groups or ethoxy groups.

2. The anti-inflammatory or anti-sunburn cosmetic composition as claimed in claim 1, wherein the cosmetically acceptable oil carrier is at least one member selected from the group consisting of vegetable oils, synthetic oils and mineral oils, and which can further contain humidity retention agents, adhesive agents, preservatives, solvents and emulsifiers.

3. The anti-inflammatory or anti-sunburn cosmetic composition as claimed in claim 1, wherein the composition further comprises an ultraviolet ray absorbing agent.

4. The anti-inflammatory or anti-sunburn cosmetic composition as claimed in claim 1, wherein the composition further comprises at least one member selected from the group consisting of antioxidants, pH regulators, cosmetic fillers, sweetening agents, coloring matters and perfumes.

* * * * *